United States Patent
Coney et al.

(10) Patent No.: US 11,286,917 B2
(45) Date of Patent: Mar. 29, 2022

(54) MOTOR DRIVE SYSTEM AND METHOD

(71) Applicant: Franklin Electric Co., Inc., Fort Wayne, IN (US)

(72) Inventors: Jason L. Coney, Fort Wayne, IN (US); Jared E. Evans, Fort Wayne, IN (US); Lyon van der Merwe, Oriel (ZA)

(73) Assignee: FRANKLIN ELECTRIC CO., INC., Fort Wayne, IN (US)

( * ) Notice: Subject to any disclaimer, the term of this patent is extended or adjusted under 35 U.S.C. 154(b) by 417 days.

(21) Appl. No.: 16/343,390

(22) PCT Filed: Oct. 20, 2017

(86) PCT No.: PCT/US2017/057692
§ 371 (c)(1),
(2) Date: Apr. 18, 2019

(87) PCT Pub. No.: WO2018/075944
PCT Pub. Date: Apr. 26, 2018

(65) Prior Publication Data
US 2019/0249650 A1  Aug. 15, 2019

Related U.S. Application Data (60) Provisional application No. 62/411,505, filed on Oct. 21, 2016, provisional application No. 62/411,507, filed on Oct. 21, 2016.

(51) Int. Cl.
*F04C 14/28* (2006.01)
*F04B 17/03* (2006.01)
(Continued)

(52) U.S. Cl.
CPC .............. *F04B 17/03* (2013.01); *F04B 47/06* (2013.01); *F04B 49/06* (2013.01); *F04B 49/065* (2013.01);
(Continued)

(58) Field of Classification Search
CPC .. F04B 17/006; F04B 2203/0207–0209; F04B 51/00; F04B 49/00; F04B 49/02;
(Continued)

(56) References Cited

U.S. PATENT DOCUMENTS 3,878,501 A * 4/1975 Moorhead .............. H01C 7/022
338/22 R
4,162,437 A    7/1979 Gray et al.
(Continued)

FOREIGN PATENT DOCUMENTS

RU    2181829    4/2002
RU    2341004    12/2008

OTHER PUBLICATIONS power.com, URL: https://www.power.com/community/forum/motor-drivers/2019/speed-physical-rotor (Year: 2019).*
(Continued)

*Primary Examiner* — Devon C Kramer
*Assistant Examiner* — Thomas Fink
(74) *Attorney, Agent, or Firm* — Faegre Drinker Biddle & Reath LLP (57) ABSTRACT

A water pumping system, a motor drive, and a method of starting pumping by the motor drive. The method includes powering the electric motor with a motor drive; driving a progressive cavity pump with the electric motor; monitoring a speed difference between an electrical speed and an observed speed of a rotor of the electric motor; and performing a protective action as a function of the speed difference.

20 Claims, 4 Drawing Sheets

(51) Int. Cl.

| | | |
|---|---|---|
| *F04B 49/06* | (2006.01) | |
| *F04C 2/107* | (2006.01) | |
| *F04C 14/08* | (2006.01) | |
| *H02P 6/06* | (2006.01) | |
| *F04C 14/06* | (2006.01) | |
| *F04B 47/06* | (2006.01) | |
| *H02P 29/10* | (2016.01) | |
| *F04B 51/00* | (2006.01) | |
| *E21B 43/12* | (2006.01) | |

(52) U.S. Cl.
CPC .......... *F04B 51/00* (2013.01); *F04C 2/1071* (2013.01); *F04C 14/06* (2013.01); *F04C 14/08* (2013.01); *F04C 14/28* (2013.01); *H02P 6/06* (2013.01); *H02P 29/10* (2016.02); *E21B 43/128* (2013.01); *F04B 2203/0209* (2013.01); *F04C 2270/025* (2013.01)

(58) Field of Classification Search
CPC ........... F04B 49/20; F04B 49/06–065; F04B 49/10–103; F04B 2201/1201–1203; F04C 2270/02–035; F04C 14/06; F04C 14/08; F04C 14/00; F04C 14/28; F04C 28/06; F04C 28/08; F04C 28/00; F04C 28/28; F04C 13/008; F04C 2210/1094; F04C 2/107–1078; H02P 29/10; H02P 29/40; H02P 29/032; E21B 43/128
USPC .............................. 417/366, 368, 372, 410.5
See application file for complete search history.

(56) References Cited

U.S. PATENT DOCUMENTS

| | | | |
|---|---|---|---|
| 5,841,260 A | 11/1998 | Imai | |
| 6,041,856 A | 3/2000 | Thrasher | |
| 6,045,333 A | 4/2000 | Breit | |
| 6,468,058 B1 | 10/2002 | Breit et al. | |
| 7,042,180 B2 | 5/2006 | Terry | |
| 7,358,694 B2 | 4/2008 | Won et al. | |
| 7,437,215 B2 | 10/2008 | Anderson | |
| 7,869,978 B2 | 1/2011 | Anderson | |
| 8,152,492 B2 | 4/2012 | Beck | |
| 10,001,121 B2 | 6/2018 | Van der Merwe | |
| 2004/0062658 A1 | 4/2004 | Beck | |
| 2006/0130481 A1 | 6/2006 | Browe | |
| 2007/0014056 A1 | 1/2007 | Andersen et al. | |
| 2007/0046227 A1* | 3/2007 | Lagier | H02K 23/66 318/268 |
| 2007/0212229 A1 | 9/2007 | Stavale | |
| 2008/0066478 A1 | 3/2008 | Okamoto et al. | |
| 2008/0067116 A1 | 3/2008 | Anderson | |
| 2008/0240932 A1 | 10/2008 | Carstensen | |
| 2009/0096398 A1 | 4/2009 | Kyrtsos et al. | |
| 2009/0292245 A1 | 11/2009 | Basso et al. | |
| 2010/0034665 A1 | 2/2010 | Zhong | |
| 2010/0288493 A1* | 11/2010 | Fielder | E21B 43/128 166/250.15 |
| 2011/0181431 A1 | 7/2011 | Koehl | |
| 2012/0003112 A1 | 1/2012 | Hayashimoto | |
| 2012/0087805 A1 | 4/2012 | Marioni | |
| 2012/0101788 A1 | 4/2012 | Kallesoe | |
| 2012/0177504 A1 | 7/2012 | Beck | |
| 2013/0106331 A1* | 5/2013 | Guzelgunler | H02P 1/46 318/400.21 |
| 2013/0151216 A1 | 6/2013 | Palka | |
| 2015/0002071 A1* | 1/2015 | Wang | H02P 21/13 318/799 |
| 2016/0115959 A1 | 4/2016 | Cheng | |
| 2016/0141912 A1* | 5/2016 | Lawrence | F04B 17/006 318/139 |
| 2017/0052208 A1* | 2/2017 | Reddy | H02P 6/16 |
| 2019/0097549 A1 | 3/2019 | Colby | |
| 2019/0271303 A1 | 9/2019 | Endo | |

OTHER PUBLICATIONS purdue.edu, URL: https://engineering.purdue.edu/~dionysis/EE452/Lab9/Lab9.pdf (Year: 2013).*

International Preliminary Report on Patentability received for PCT Patent Application No. PCT/US2017/057692, dated May 2, 2019, 8 pages.

International Search Report and Written Opinion received for PCT Patent Application No. PCT/US2017/057692, dated Jan. 2, 2018, 9 pages.

* cited by examiner

MOTOR DRIVE SYSTEM AND METHOD

CROSS-REFERENCE TO RELATED APPLICATIONS

The present application is a § 371 National Stage entry of International Application No. PCT/US2017/057692 titled MOTOR DRIVE SYSTEM AND METHOD, filed on Oct. 20, 2017, which claims the benefit of priority from U.S. Provisional Patent Applications Nos. 62/411,505 and 62/411,507, both filed Oct. 21, 2016, said applications incorporated by reference herein in their entirety.

FIELD OF THE DISCLOSURE

The disclosure relates generally to a system and a method for driving a motor. More particularly, the disclosure relates to a system and method for adaptively controlling an operating characteristic of the motor in a fluid pumping system.

BACKGROUND OF THE DISCLOSURE

Fluid pumping systems use motors to drive pumps and transfer fluids from supply reservoirs such as wells. A sensor measures a characteristic of the fluid, and a motor drive controls the motor to maintain the characteristic near its setpoint. In some systems, the motor drive measures pressure in a fluid circuit and controls the speed of the motor to maintain the pressure near its setpoint.

The pump must operate against the well head. Wells can be deep or shallow, and the fluid level within each well varies. The pump pressure can therefore be significantly higher than the pressure sensed by the pressure sensor. The pump pressure can vary significantly between installations and also within the same installation as the level of the fluid in the well rises or falls.

Pumping systems can be used in developed and developing countries to pump water, often in remote locations. In many applications it is desirable to provide a low cost system that is simple to use and does not require calibration or tuning by the user. Low cost and simple systems are typically more reliable as they have fewer complexities, which further enhances their value.

Due to their construction, progressive cavity pumps have a high starting friction, or stiction, and are known to suffer permanent degraded performance when various operating conditions are exceeded. Physical sensors external to the motor drive powering the pump can be deployed to monitor flow, pressure, and temperature. But external sensors are prone to failure and malfunction and replacing them can be inconvenient.

It is desirable to find new ways to protect progressive cavity pumps to maintain a high level of performance and prevent catastrophic failures.

SUMMARY

Embodiments of a water pumping system, a motor drive, and a method of operating an electric motor with the motor drive are disclosed. In some embodiments, the method comprises: powering the electric motor with a motor drive; driving a progressive cavity pump with the electric motor; monitoring a speed difference between an electrical speed and an observed speed of a rotor of the electric motor; and performing a protective action as a function of the speed difference.

In some embodiments, a motor drive is configured to operate a progressive cavity pump in a water pumping system, and comprises a controller configured to perform a method comprising: powering the electric motor with the motor drive; driving the progressive cavity pump with the electric motor; monitoring a speed difference between an electrical speed and an observed speed of a rotor of the electric motor; and performing a protective action as a function of the speed difference.

In some embodiments, a water pumping system comprises a progressive cavity pump; an electrical motor coupled to the progressive cavity pump; and a motor drive to power the electrical motor, the motor drive configured to drive the progressive cavity pump and including a controller configured to perform a method comprising: powering the electric motor with the motor drive; driving the progressive cavity pump with the electric motor; monitoring a speed difference between an electrical speed and an observed speed of a rotor of the electric motor; and performing a protective action as a function of the speed difference.

DESCRIPTION OF THE DRAWINGS

The features and advantages of the disclosure will become more readily appreciated as the same become better understood by reference to the following detailed description when taken in conjunction with the accompanying drawings, where.

Corresponding reference characters indicate corresponding parts throughout the several views. Although the drawings represent embodiments of various features and components according to the present invention, the drawings are not necessarily to scale and certain features may be exaggerated in order to better illustrate and explain the present invention.

DETAILED DESCRIPTION OF DISCLOSED EMBODIMENTS

For the purpose of promoting an understanding of the principles of the invention, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended.

Except where a contrary intent is expressly stated, terms are used in their singular form for clarity and are intended to include their plural form.

As used herein, the terms "comprising," "containing," "having" and "including" denote an open transition meaning that the claim in which the open transition is used is not limited to the elements following the terms "comprising" or "including". By contrast, the terms "consisting of" or "consists of" denote closed transitions.

Occurrences of the phrase "in one embodiment," or "in one aspect," herein do not necessarily all refer to the same embodiment or aspect.

Helical rotor pumps are well known to suffer permanent degraded performance when various operating conditions are exceeded, which can include overpressure conditions, dry running conditions, over-speed conditions, stall conditions, and over-power conditions. Problems may result from overheating or running dry. For example rubber seals may deform or melt as a result of heat and high torque, or excessive striction. Improved control logic is provided herein which considers the difference between electrical and mechanical rotor speeds of the motor driving the helical rotor pump to determine whether the helical rotor pump is operating safely.

A helical rotor pump is a type of progressive cavity pump. Progressive cavity pumps also include centrifugal pumps. Progressive cavity pump and helical rotor pump are used interchangeably herein. Progressive cavity pumps are also known as cavity pumps and eccentric screw pumps.

Figure 1:
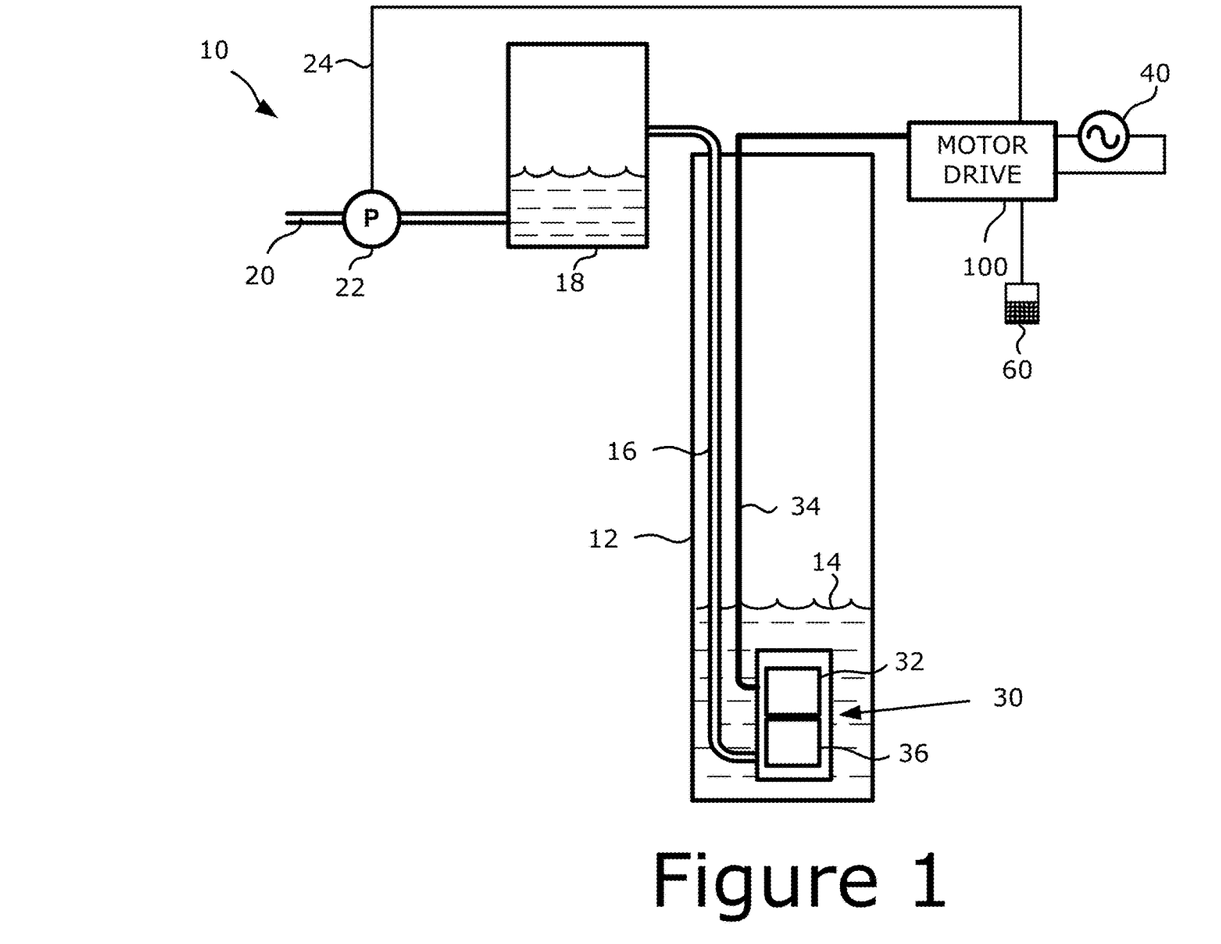
FIG. 1 is a diagrammatic representation of an embodiment of a liquid supply system.

The foregoing exemplary embodiments of the disclosure will now be described with reference to the figures. Referring to FIG. 1, a diagrammatic representation of a liquid supply system 10 is disclosed. Example liquids include water, gasoline fuel, diesel fuel, petroleum, oil, sewage, and combinations of such liquids with gases and solids, such as water and coal-based methane gas. Although the embodiments below may be described with reference to water, the invention is not so limited and the principles and advantages thereof may be applicable to any liquid. The liquid supply system comprises a reservoir 12 containing water 14 which is pumped by a pump unit 30 through a conduit 16, optionally via a reservoir 18, e.g. a pressure tank, to a conduit 20 of a closed system. Pump unit 30 includes a pump 36 driven by a motor 32 which is powered by a motor drive 100 via power conductors 34. The size of reservoir 12, which is interposed between pump unit 30 and a pressure sensor, affects the response of the system. In one example, motor drive 100 is a variable frequency drive (VFD) and pump 36 is a helical rotor pump. Power conductors 34 may comprise two or more wires to provide single or three phase power to motor 32.

During operation of the system, water 14 flows out of conduit 20. For example, the system may be a water system in a home, in which case water flows out of conduit 20 when a faucet is opened or an irrigation system is turned on. Constant pressure ensures the heads of the irrigation system spray at a constant distance from the head to provide even and predictable irrigation. Fluid characteristics including pressure may be monitored with a pressure sensor 22 disposed in conduit 20 to generate a pressure signal useful to maintain pressure about a setpoint. The pressure signal is provided via line 24 connecting pressure sensor 22 and motor drive 100. An exemplary input device 60 is also shown. Input device 60 is provided to receive, from a user, input parameters such as setpoints and schedules. Input device 60 may comprise a smart device wirelessly coupled to motor drive 100. Example smart devices include computers, smart phones and tablets. Smart devices may also be connected remotely via radio signal. Reservoir 12 may be an aboveground or underground tank, a well casing, or any other reservoir containing water 14.

Figure 2:
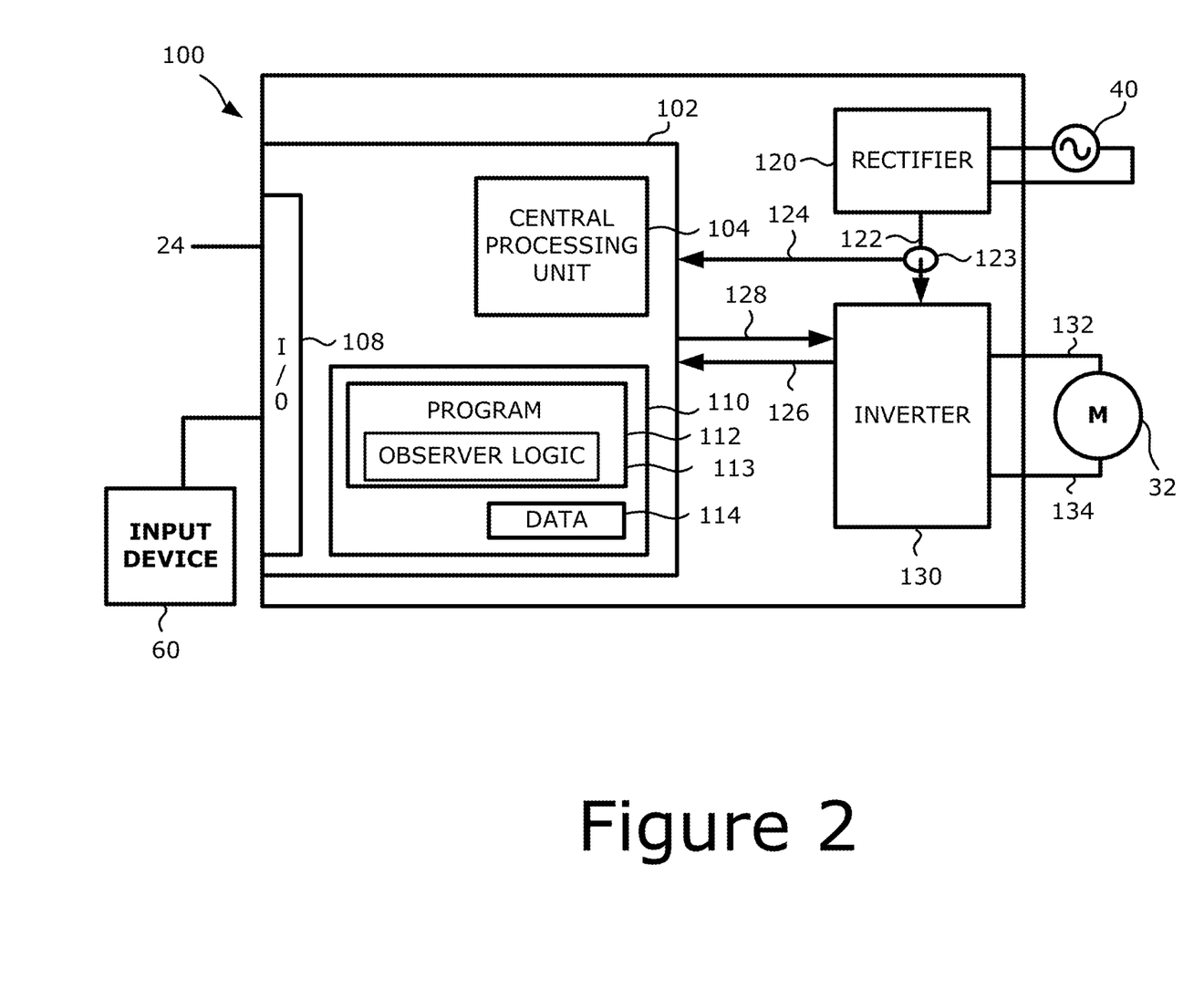
FIG. 2 is a block diagram of an embodiment of a motor drive.

FIG. 2 illustrates an embodiment of motor drive 100 comprising a processing device, illustratively controller 102, a rectifier 120 and an inverter 130. As shown, controller 102 includes a CPU 104 configured to access a memory device 110 and execute processing instructions from a software application, exemplified by program 112, based on data 114. Techniques for generating motor voltages according to characteristics of a control signal are known in the art. In one example, a technique comprises storing values in a table corresponding to samples of an operating curve. The operating curve is typically a substantially straight line defining a volts-hertz relationship. Other relationships between volts and hertz can also be accommodated. When the speed control system determines a desired operating speed, which defines an operating frequency, the motor drive looks up a voltage corresponding to the frequency. The motor drive then generates a motor voltage based on the voltage and the frequency. In another example, a formula or a function embodying the operating curve characteristics is used by CPU 104 to generate the desired motor voltages.

Rectifier 120 is powered by a power source 40 and includes any rectification circuit well known in the art, e.g. a diode bridge, to convert alternating-current (AC) voltage supplied by power source 40 into direct-current (DC) voltage which it supplies to inverter 130. Inverter 130 receives DC power from rectifier 120 through a conductor 122 and converts the DC power into an AC motor power.

CPU 104 receives inputs through an I/O interface 108 and outputs a control signal over line 128 to inverter 130. In one example, the control signal is provided to a pulse-width-modulated (PWM) module having power switches and control logic which generates the appropriate gating signals for the power switches to convert the DC power supplied by rectifier 120 to the AC motor voltage suitable to drive the motor according to the control signal, provided to the motor via conductors 132, 134. Current drawn by inverter 130 from rectifier 120 is sensed by a current sensor 123 and a current signal is provided by current sensor 123 to CPU 104 by conductor 124. Motor voltage feedback can also be provided, for example through conductor 126 connecting inverter 130 and controller 102. Motor voltages may also be generated with other known or later developed drive topologies programmed in accordance with embodiments of the disclosure.

In another embodiment, the system may be a drinking water system in a feedlot and power source 40 may be a renewable energy source powering motor drive 100. Examples of renewable energy sources include solar energy, wind energy, and hydroelectric energy. Reservoir 18 may be sufficiently large to store enough water to supply the animals in the feedlot when renewable energy is low or nonexistent for a period of time. For example, reservoir 18 may store enough water to supply the animals in the feedlot from dusk to dawn, particularly since during this time animals do not require as much water as they do during daytime. Power source 40 in the present embodiment may comprise voltage or current regulators, step-up or step-down converters, and any devices known in the art for conditioning power incoming from the renewable energy source to match the motor drive input requirements. Furthermore, if the renewal energy source generates variable DC power, e.g. solar energy panels, rectifier 120 may be omitted and power source 40 may be coupled to inverter 130.

In a more general embodiment, the controller comprises control logic operable to generate the control signal. The term "logic" as used herein includes software and/or firmware executing on one or more programmable processors, application-specific integrated circuits, field-programmable gate arrays, digital signal processors, hardwired logic, or combinations thereof. Therefore, in accordance with the embodiments, various logic may be implemented in any appropriate fashion and would remain in accordance with the embodiments herein disclosed. A non-transitory machine-readable medium comprising logic can additionally be considered to be embodied within any tangible form of a computer-readable carrier, such as solid-state memory, magnetic disk, and optical disk containing an appropriate set of computer instructions and data structures that would cause a processor to carry out the techniques described herein. A non-transitory computer-readable medium, or memory, may include random access memory (RAM), read-only memory (ROM), erasable programmable read-only memory (e.g., EPROM, EEPROM, or Flash memory), or any other tangible medium capable of storing information.

In a motor driven by a variable frequency drive, torque may be calculated as follows:

$$T = \frac{\sqrt{3} \times V \times I \times PF}{\omega}$$

$T$ – Torque $V$ – Voltage $I$ – Current $PF$ – Power Factor $\omega$ – rotational speed The torque also has a proportional relationship to the motor's current and is influenced by the actual operating point as well. As an illustration, the current is also influenced by the speed or rather total load on the shaft. Additionally, the load and magnetization component of the current are to be separated so that the load component can be used to establish the correlation. Accordingly, a desired torque level can be caused by controlling the voltage and current according to the present load.

Figure 3:
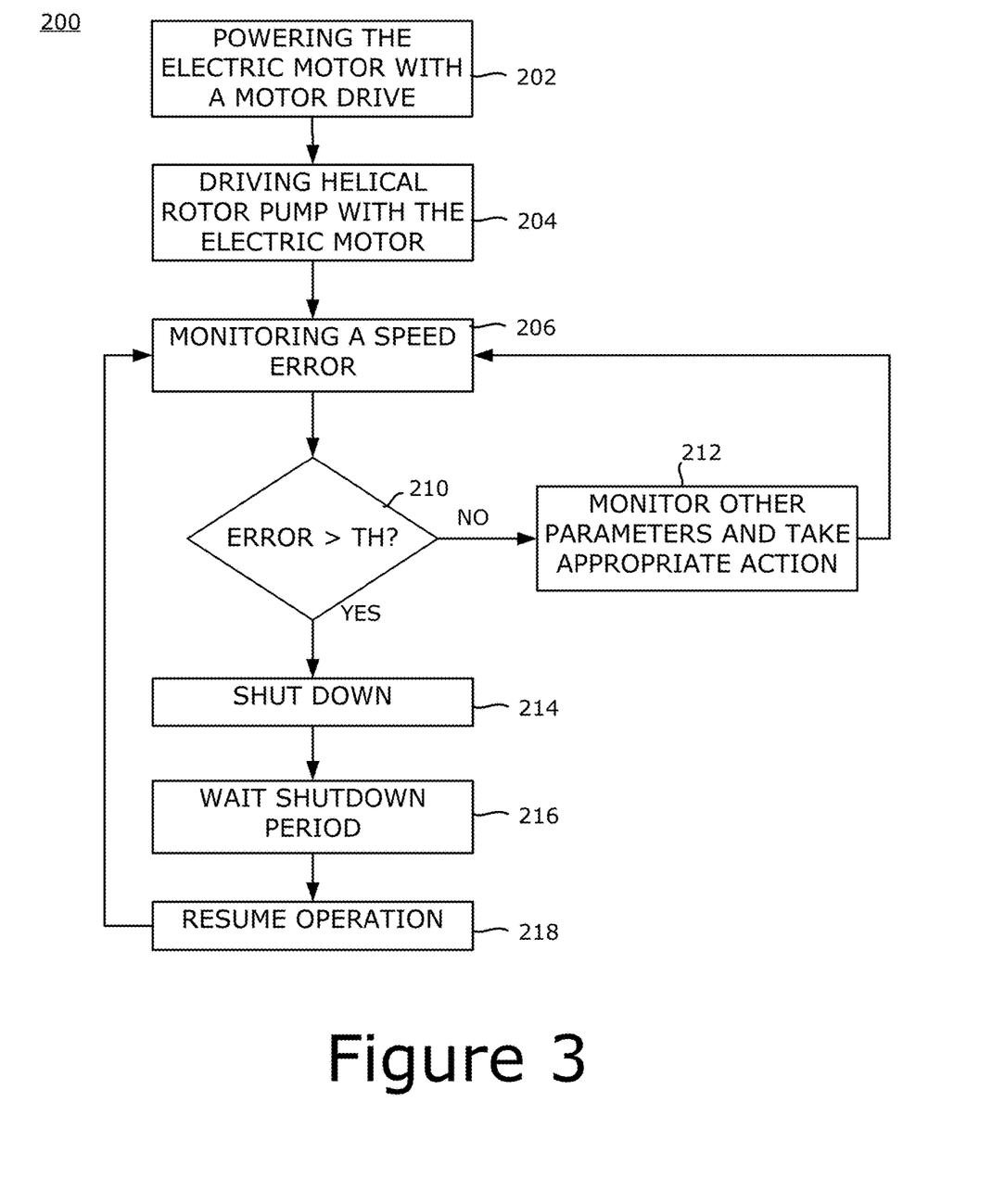
FIG. 3 is a flowchart depicting an embodiment of a protection method for a progressive cavity pump.
Figure 4:
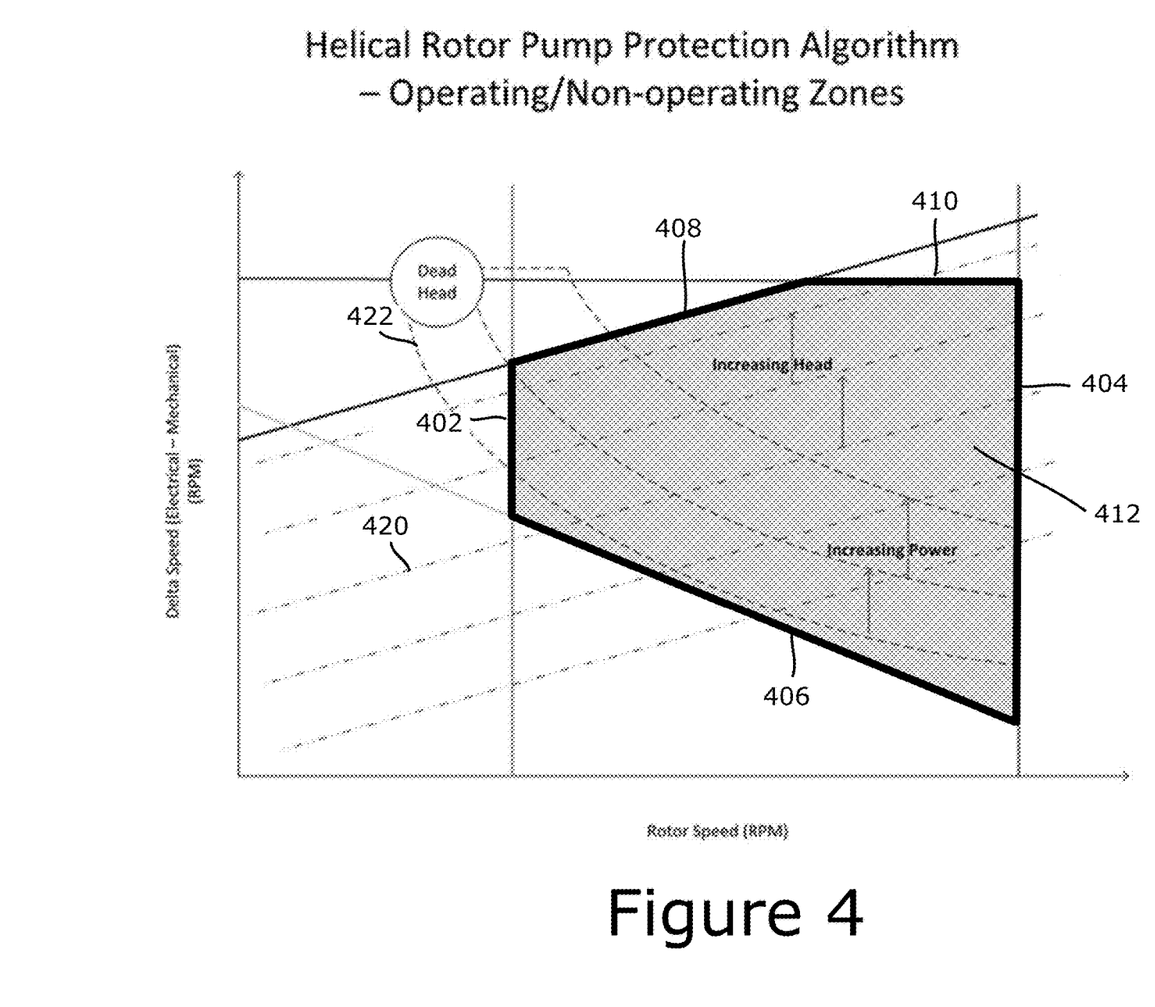
FIG. 4 is a graph provided to illustrate the functionality of control logic embodied in the method described with reference to FIG. 3.

Referring now to FIG. 3, a flowchart 200 is provided to depict an embodiment of a method to adaptively control an operating characteristic of a motor in a fluid pumping system. The operating characteristic may be voltage, current, power, or torque, and may be controlled indirectly by controlling one or more of voltage, current, and power. The method can be implemented with a motor drive such as motor drive 100 described with reference to FIG. 2. FIG. 4 is a graph provided to illustrate the functionality of control logic embodied in the method described with reference to FIG. 3. FIG. 4 illustrates an operating zone 412 defined by a minimum speed 402, a maximum speed 404, a minimum power 406, an over-torque trip or limit 408, and a dry well trip or limit 410. These boundaries of operating zone 412 represent a safe operating area of the system. Protective actions, such as stopping the motor or reducing its speed, may be performed to protect the motor or the pump as a function of the difference between the electrical and mechanical, or observed, speeds of the motor. Constant head lines 420 and constant power lines 422 are also shown. Operation outside operating 412 is undesirable. The speed error (described below) is shown on the vertical axis and the observed speed (described below) is shown on the horizontal axis. In various embodiments described below, the motor drive will not allow the motor to operate outside operating zone 412 for a sustained period of time. For example, the motor drive will not operate the motor for a sustained period of time above the maximum speed or minimum speed limits.

The method comprises, at 202, powering the electric motor with a motor drive; driving, at 204, a progressive cavity pump with the electric motor; and monitoring, at 206, a speed error. The speed error is a speed difference between an electrical speed and an observed speed of a rotor of the electric motor, also describable as the difference between the electrical speed and the mechanical speed of the motor. The error reflects the rotor's inability to maintain the commanded speed, indicated by the electrical speed. Algorithms to determine observed speed based on current, known as "observers," are well known in the art. Accordingly, the motor drive may be said to operate in a sensorless manner. Alternatively, the speed of the motor may be determined by sensing the rotation speed of the rotor or sensing a mechanically linked device whose speed correlates to the speed of the rotor.

The method continues, at 210, with comparing the speed error to an error threshold. If the error threshold is exceeded, the method continues by performing a corrective action. The error threshold corresponds to a maximum speed difference 410, shown in FIG. 4. An example corrective action is illustrated at 214, shutting down the motor drive. If the threshold is not exceeded, the motor drive proceeds at 212 to monitor other parameters and take appropriate action. Monitoring of other parameters and the speed error is performed substantially continuously and may be performed in any order.

At 216, the motor drive waits a shutdown period and at 218 the motor drive resumes operation.

In one variation of the present embodiment, the motor drive generates a motor voltage having a variable frequency, and the electrical speed corresponds to the variable frequency. In one example, the motor drive comprises closed loop observer logic 113 (shown in FIG. 2) configured to determine the observed speed. The closed loop observer logic determines the observed speed responsive to disturbances in a feedback current corresponding to a current drawn by the electrical motor.

In another variation of the present embodiment, the method further comprises monitoring a minimum power boundary 406 as a function of the observed speed and the speed difference; and performing the protective action responsive to the speed difference remaining below a speed difference corresponding to the minimum power boundary as a function of the observed speed, for a first time period. The foregoing variation is illustrated in FIG. 4 with reference to operating points 430 and 432. Operating point 430 is below minimum power boundary 406 for a given speed error or difference denoted by the dashed line connecting operating point 430 to operating point 432, which is above minimum power boundary 406. Also, operating point 430 occurs at a slower observed speed than operating point 432. Operating point 430 is outside safe zone 412 and thus triggers a protective action. Operating point 432 is inside safe zone 412 and thus does not trigger a protective action.

In another variation of the present embodiment, the method further comprises monitoring a maximum torque boundary 408 as a function of the observed speed and the speed difference; and performing the protective action responsive to the speed difference remaining above a speed difference corresponding to the maximum torque boundary as a function of the observed speed, for a second time period. The second time period may be the same or different from the first time period. The foregoing variation is illustrated in FIG. 4 with reference to operating points 434 and 436. Operating point 434 is above maximum torque boundary 408 for a given speed error or difference denoted by the dashed line connecting operating point 434 to operating point 436, which is not above maximum torque boundary 408. Also, operating point 434 occurs at a slower observed speed than operating point 436. Operating point 434 is outside safe zone 412 and thus triggers a protective action. Operating point 436 is inside safe zone 412 and thus does not trigger a protective action.

In another variation of the present embodiment, the method further comprises monitoring a maximum torque boundary 408 between the observed speed and the speed difference; and performing the protective action responsive to the speed difference remaining above the maximum torque boundary at any corresponding observed speed, for a second time period.

In another variation of the present embodiment, the method further comprises performing the protective action responsive to the observed speed exceeding a maximum speed limit, for a third time period.

In another variation of the present embodiment, the method further comprises performing the protective action responsive to the observed speed being below a minimum speed limit, for a fourth time period.

In another variation of the present embodiment, the method further comprises monitoring a safe operating zone defined by boundaries consisting of a minimum speed limit, a maximum speed limit, a maximum torque boundary, and a minimum power boundary; and if the speed difference is below a maximum speed difference 410, performing the protective action responsive to the speed difference and the observed speed indicating that one of the boundaries has been crossed for a time period corresponding to the one of the boundaries that has been crossed. In one example, if more than one of the boundaries has been crossed, the method further comprises performing the protective action as soon as the first of the time periods expires. As each boundary may have an associated time period (first through fourth time periods above) which may be the same or different, the first boundary crossing may have a longer time period than the next boundary crossing, therefore the time period of the "next" boundary crossing may expire first and cause the protective action to occur even if the time period of the first boundary crossing has not expired. Performing the protective action comprises ceasing operation of the motor drive and resuming operation of the motor drive responsive to the lapse of a timeout period.

In some embodiments, a motor drive configured to operate a progressive cavity pump in a water pumping system comprises a controller including control logic configured to perform the method described with reference to FIG. 3 and any one or more of the variations thereof described in the foregoing paragraphs. Accordingly, the motor drive may be said to operate in a sensorless manner.

In some embodiments, a water pumping system comprises a progressive cavity pump; an electrical motor coupled to the progressive cavity pump; and a motor drive to power the electrical motor, the motor drive configured to drive the progressive cavity pump and including a controller comprising control logic configured to perform the method described with reference to FIG. 3 and any one or more of the variations thereof described in the foregoing paragraphs.

In one variation, the system further comprises a solar array electrically coupled to supply power to the motor drive.

Unless otherwise expressly stated in connection with a specific use thereof, the term "device" includes a single device, a plurality of devices, two components integrated into a device, and any variations thereof. The singular form is only used to illustrate a particular functionality and not to limit the disclosure to a single component. Therefore, a controller includes, for example, a central processing unit, a math processing unit, a plurality of processors on a common integrated circuit, and a plurality of processors operating in concert, whether physically or electronically coupled. Furthermore, the term "program" includes a single application, a plurality of applications, one or more subroutines, software, firmware, and any variations thereof suitable to execute instruction sequences with a controller.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of operating an electric motor, the method comprising:
   powering the electric motor with a motor drive;
   driving a progressive cavity pump with the electric motor;
   monitoring a speed difference between an electrical speed and an observed speed of a rotor of the electric motor; and
   performing a protective action as a function of the speed difference,
   wherein performing the protective action as a function of the speed difference comprises performing the protective action responsive to the speed difference remaining:
   (A) below a speed difference corresponding to a minimum power boundary as a function of the observed speed, for a first time period, or
   (B) above a speed difference corresponding to a maximum torque boundary as a function of the observed speed, for a second time period.

2. The method of claim 1, further comprising performing the protective action as a function of the speed difference comprises performing the protective action responsive to the speed difference reaching or exceeding a maximum speed difference.

3. The method of claim 1, wherein the motor drive generates a motor voltage having a variable frequency, and wherein the electrical speed corresponds to the variable frequency.

4. The method of claim 2, wherein the motor drive comprises closed loop observer logic configured to determine the observed speed.

5. The method of claim 3, wherein the closed loop observer logic determines the observed speed responsive to disturbances in a feedback current corresponding to a current drawn by the electrical motor.

6. The method of claim 1, wherein between a minimum speed boundary and a maximum speed boundary the minimum power boundary decreases as the observed speed increases.

7. The method of claim 6, wherein the minimum power boundary decreases linearly between the minimum speed boundary and the maximum speed boundary.

8. The method of claim 1, wherein the maximum torque boundary increases as the observed speed increases.

9. The method of claim 8, wherein the maximum torque boundary increases linearly between a minimum speed boundary and a maximum speed difference.

10. A method of operating an electric motor, the method comprising:

powering the electric motor with a motor drive;
driving a progressive cavity pump with the electric motor;
monitoring a speed difference between an electrical speed and an observed speed of a rotor of the electric motor;
performing a protective action as a function of the speed difference, wherein performing the protective action as a function of the speed difference comprises:
monitoring a maximum torque boundary between the observed speed and the speed difference; and
performing the protective action responsive to the speed difference remaining above the maximum torque boundary at any corresponding observed speed for a second time period.

11. The method of claim 1, further comprising performing the protective action responsive to the observed speed exceeding a maximum speed limit for a third time period.

12. The method of claim 1, further comprising performing the protective action responsive to the observed speed being below a minimum speed limit for a fourth time period.

13. A method of operating an electric motor, the method comprising:
powering the electric motor with a motor drive;
driving a progressive cavity pump with the electric motor;
monitoring a speed difference between an electrical speed and an observed speed of a rotor of the electric motor; and
performing a protective action as a function of the speed difference,
wherein performing the protective action as a function of the speed difference comprises:
monitoring a safe operating zone defined by boundaries consisting of a minimum speed limit, a maximum speed limit, a maximum torque boundary, and a minimum power boundary; and
if the speed difference is below the maximum speed difference, performing the protective action responsive to the speed difference and the observed speed indicating that one of the boundaries has been crossed for a time period corresponding to the one of the boundaries that has been crossed.

14. The method of claim 13, wherein if more than one of the boundaries has been crossed, the method further comprises performing the protective action responsive to earliest to expire time period.

15. The method of claim 1, wherein performing the protective action comprises ceasing operation of the motor drive; and resuming operation of the motor drive responsive to the lapse of a timeout period.

16. A motor drive configured to operate a progressive cavity pump in a water pumping system, the motor drive comprising a controller configured to perform a method comprising:
powering an electric motor with the motor drive;
driving the progressive cavity pump with the electric motor;
monitoring a speed difference between an electrical speed and an observed speed of a rotor of the electric motor; and
performing a protective action as a function of the speed difference,
wherein performing a protective action as a function of the speed difference comprises:
monitoring a safe operating zone defined by boundaries consisting of a minimum speed limit, a maximum speed limit, a maximum torque boundary, and a minimum power boundary; and
if the speed difference is below the maximum speed difference, performing the protective action responsive to the speed difference and the observed speed indicating that one of the boundaries has been crossed for a time period corresponding to the one of the boundaries that has been crossed.

17. The method of claim 10, further comprising performing the protective action responsive to the observed speed (a) exceeding a maximum speed limit for a third time period or (b) being below a minimum speed limit for a fourth time period.

18. The method of claim 13, further comprising performing the protective action responsive to the observed speed (a) exceeding a maximum speed limit for a third time period or (b) being below a minimum speed limit for a fourth time period.

19. The motor drive of claim 16, wherein the controller is further configured to perform the protective action responsive to the observed speed (a) exceeding a maximum speed limit for a third time period or (b) being below a minimum speed limit for a fourth time period.

20. The method of claim 16, wherein performing the protective action comprises ceasing operation of the motor drive; and resuming operation of the motor drive responsive to the lapse of a timeout period.

\* \* \* \* \*